(12) United States Patent
Gindrat et al.

(10) Patent No.: US 10,070,663 B2
(45) Date of Patent: Sep. 11, 2018

(54) EVALUATING POROSITY DISTRIBUTION WITHIN A POROUS ROD

(71) Applicant: PHILIP MORRIS PRODUCTS S.A., Neuchatel (CH)

(72) Inventors: Pierre-Yves Gindrat, Saxon (CH); Karl Markus Nordlund, St-Sulpice (CH); Yorick Klipfel, St-Saphorin-sur-Morges (CH)

(73) Assignee: Philip Morris Products S.A., Neuchatel (CH)

( * ) Notice: Subject to any disclaimer, the term of this patent is extended or adjusted under 35 U.S.C. 154(b) by 392 days.

(21) Appl. No.: 14/766,896

(22) PCT Filed: Feb. 13, 2014

(86) PCT No.: PCT/EP2014/052861
§ 371 (c)(1),
(2) Date: Aug. 10, 2015

(87) PCT Pub. No.: WO2014/125049
PCT Pub. Date: Aug. 21, 2014

(65) Prior Publication Data
US 2015/0374028 A1 Dec. 31, 2015

(30) Foreign Application Priority Data
Feb. 13, 2013 (EP) .................................... 13155127

(51) Int. Cl.
*A24C 5/34* (2006.01)
*G06T 7/00* (2017.01)
(Continued)

(52) U.S. Cl.
CPC .......... *A24C 5/3412* (2013.01); *A24D 3/0229* (2013.01); *A24D 3/0295* (2013.01);
(Continued)

(58) Field of Classification Search
CPC ... G06T 7/181; G06T 7/62; G06T 7/11; G06T 7/004; A24D 3/0229; A24D 3/0295
See application file for complete search history.

(56) References Cited

U.S. PATENT DOCUMENTS 5,235,649 A 8/1993 Reda
5,581,370 A 12/1996 Fuss et al.
(Continued)

FOREIGN PATENT DOCUMENTS

CN 1280541 A 1/2001
CN 1105061 C 4/2003
(Continued)

OTHER PUBLICATIONS

Combined Chinese Office Action and Search Report dated Mar. 15, 2017 in Patent Application No. 201480008589.8 (English Translation only).
(Continued)

*Primary Examiner* — Pho M Luu
(74) *Attorney, Agent, or Firm* — Oblon, McClelland, Maier & Neustadt, L.L.P.

(57) ABSTRACT

A method is provided for evaluating porosity distribution within a porous article such as a crimped filter, a tobacco plug, or a cigarette, including obtaining a digital image of a transverse area of the article and determining a pore area fraction for each of a plurality of identically dimensioned sub-areas of the transverse area of the article. This provides a plurality of pore area fractions. The plurality of pore area fractions allow the evaluation of a local porosity distribution within the transverse area of the porous article. Each sub-area within which a pore area fraction is calculated overlaps with at least one adjacent sub-area by between 10% and
(Continued)

95%. The method for quantitatively evaluating porosity distribution may be used to control a process for manufacturing the porous article.

28 Claims, 5 Drawing Sheets (51) Int. Cl.
*A24D 3/02* (2006.01)
*G01N 15/08* (2006.01)
*G05B 19/4097* (2006.01)
*H04N 5/225* (2006.01)
*G06T 7/11* (2017.01)
*G06T 7/62* (2017.01)
*G06T 7/181* (2017.01)

(52) U.S. Cl.
CPC ....... *G01N 15/088* (2013.01); *G05B 19/4097* (2013.01); *G06T 7/0004* (2013.01); *G06T 7/11* (2017.01); *G06T 7/181* (2017.01); *G06T 7/62* (2017.01); *H04N 5/2256* (2013.01); *G06T 2207/10004* (2013.01); *G06T 2207/30108* (2013.01)

(56) References Cited

U.S. PATENT DOCUMENTS

| | | | |
|---|---|---|---|
| 6,171,684 B1 | 1/2001 | Kahlbaugh et al. | |
| 6,407,807 B1 | 6/2002 | Focke et al. | |
| 6,531,693 B1 | 3/2003 | Focke et al. | |
| 8,381,738 B2 * | 2/2013 | Luan | A24D 3/166 131/207 |
| 8,905,042 B2 * | 12/2014 | Zhang | A24D 3/163 131/331 |
| 2001/0003082 A1 | 6/2001 | Kahlbaugh et al. | |
| 2003/0054154 A1 * | 3/2003 | Chen | B01D 39/2068 428/305.5 |
| 2003/0167742 A1 | 9/2003 | Kahlbaugh et al. | |
| 2005/0210844 A1 | 9/2005 | Kahlbaugh et al. | |
| 2007/0052795 A1 | 3/2007 | Swanger et al. | |

FOREIGN PATENT DOCUMENTS

| | | |
|---|---|---|
| CN | 101403683 A | 4/2009 |
| CN | 102542293 A | 7/2012 |
| CN | 102866080 A | 1/2013 |
| DE | 19753333 A1 | 6/1999 |
| DE | 10 2012 210 031 A1 | 12/2013 |
| EP | 0 518 141 A3 | 12/1992 |
| EP | 0518141 A2 | 12/1992 |
| EP | 0 617 272 A1 | 9/1994 |
| EP | 0747855 A2 | 12/1996 |
| GB | 2480065 A | 11/2011 |
| JP | 08-164521 A | 6/1996 |
| JP | 10-62354 A | 3/1998 |
| JP | 2001-524425 A | 12/2001 |
| JP | 2005-520123 A | 7/2005 |
| WO | WO 2010/060001 A1 | 5/2010 |

OTHER PUBLICATIONS

Russian Search Report dated Oct. 4, 2017 in Patent Application No. 2015138962 (with English language translation).

Wolfgang Trinkies, et al., "X-Ray Absorption Analysis by Image Processing Techniques," SPIE, vol. 1027, XP055068616, Mar. 2, 1988, pp. 226-231.

International Search Report and Written Opinion dated May 9, 2014 in PCT/EP2014/052861 filed Feb. 13, 2014.

Office Action dated Dec. 4, 2017 in Japanese Patent Application No. 2015-557434 with English translation, 5 pages.

Combined Office Action and Search Report dated Feb. 21, 2018 in Taiwanese Patent Application No. 103105093 (with English language translation), 15 pages.

Taiwanese Office Action and Search Report with English translation dated Jul. 6, 2018 in corresponding Taiwanese Patent Application No. 103105093, citing documents AO and AP therein (11 pages).

* cited by examiner

EVALUATING POROSITY DISTRIBUTION WITHIN A POROUS ROD

CROSS REFERENCE TO RELATED APPLICATION

This application is a U.S. national phase application under 35 U.S.C. § 371 of PCT/EP2014/052861, filed on Feb. 13, 2014, and claims the benefit of priority under 35 U.S.C. § 119 from prior EP Application No. 13155127.7, filed on Feb. 13, 2013, the entire contents of each of which are incorporated herein by reference.

The specification relates to a method for evaluating pores within a porous article. The specification may relate in particular to a method for evaluating porosity distribution within the body of a smoking article such as a cigarette, or the porosity distribution within a rod formed from a gathered sheet of material, such as a filter.

Filters for use in smoking articles may be formed for instance by a process of crimping a sheet of suitable material, and then gathering the material together to form a continuous rod with pores along the longitudinal axis of the filter rod. The rod may then be severed at appropriate lengths to form individual filter rod segments. The nature of the process means that a filter rod segment may have a substantially uniform weight distribution of material over the rod length. Furthermore, a set of filter segments produced by the method may have a very narrow weight distribution if they are cut to the same length. Even if the density and thickness of the sheet material used to form the filter rods is substantially uniform over the width of the sheet such that variations in overall porosity between filters is small, the morphology of the crimped and gathered sheet within the filter can vary greatly, resulting in large variations in the distribution of pore area fractions over the cross-section of the filter. The cross-sectional distribution of pore area fractions of a porous article, such as a crimped and gathered filter, may conveniently be referred to as "porosity distribution" or "local porosity distribution". The width of the porosity distribution may be represented by the standard deviation in a plurality of pore area fractions. In general, the porosity distribution measured according the present invention will be most representative of the entire porous article if the pores have the same size and morphology throughout the length of the porous article.

Such variations in the porosity distribution may influence the efficacy of the filter greatly. As an example, if the sheet material is gathered into the rod such that a portion of the cross-section of the rod has virtually no porosity, and a different portion of the cross-section of the rod has almost 100% porosity, then the filter may not function as intended. Properties such as resistance to draw may also be strongly influenced by the local porosity distribution.

Some smoking articles, for example heated aerosol-generating articles, may comprise tobacco plugs formed by crimping and gathering a sheet of processed tobacco material into a continuous rod, and severing the rod at appropriate lengths to form individual tobacco plugs. The structure of a tobacco plug formed in this way may be similar to the structure of a filter produced by crimping and gathering a sheet of appropriate filter material. It is desirable that there is low variability of physical properties from one tobacco plug to another. The plugs in a batch of plugs each preferably have similar weight so that they contain similar amounts of tobacco material, and each should also have similar internal morphology. The morphology of the tobacco plug can be important for determining how well it functions within a heated aerosol-generating smoking article.

Conventional cigarettes may be formed by producing a continuous rod of cut tobacco wrapped in a cigarette paper, and then severing the continuous rod at appropriate lengths to form individual tobacco sticks or tobacco rods in the form of cigarettes. It is typical for a filter to be applied to one end of a tobacco rod to form the final cigarette product. At least one end of the cigarette is a loose end, or an open end, and the cut tobacco contained within the body of the rod may fall out of the rod at this end. If a cigarette is not formed with the correct density of cut tobacco, material may be more likely to fall out the open end, and such a cigarette would be of low quality. One way of evaluating the amount of material that has fallen out at the end of the cigarette may be to evaluate the porosity distribution of the cigarette at the open end.

A methodology for determining uniformity of porosity distribution within a porous article, such as a porous rod, may be useful in quantitatively determining and controlling the quality of products such as filters, tobacco plugs, and cigarettes.

EP0518141 discloses a method for determining when a cigarette in a bundle is unsuitable, for example being improperly filled, broken or short. The method disclosed measures the luminescence off the end faces from a bundle of conventional cigarettes. The generated signal corresponding to the amount of light received by each pixel of a light sensitive sensor (i.e., CCD) is measured, and adjusted on a grey-scale from 0-255. The grey-scale adjusted measured signal from each pixel is plotted and the standard deviation of the luminescence measured from the bundle of cigarettes is calculated to provide a threshold to determine whether or not to reject the entire bundle. EP0518141 does not determine uniformity of porosity distribution.

DE19753333 discloses a method for determining whether batches of cigarettes are sufficiently filled. Signal intensity representative of front-ends of a batch of cigarettes is measured using a CCD camera. The number of adjacent pixels below a certain threshold are deemed as indicators of areas with inadequately filled cigarettes. DE19753333 does not disclose a way to differentiate between pores that are uniformly distributed throughout a tobacco rod and one where all the pores have coalesced into one large pore or one large area of an inadequately filled cigarette.

EP0747855 discloses a method of enhancing a digital image. Multiple local histograms are created to improve visual local contrast within a subarea of a natural scene image.

In one aspect, a quantitative method for evaluating porosity distribution within a porous article, such as a porous rod, comprises the steps of obtaining a digital image of a transverse area of the article, determining the pore area fraction present within each of a plurality of identically dimensioned sub-areas of the transverse area of the article, thereby obtaining a plurality of pore area fractions, and using the plurality of pore area fractions to evaluate the cross-sectional distribution of pore area fractions within the transverse area of the article, which will also be referred to herein as the porosity distribution. Each sub-area overlaps at least one adjacent sub-area, preferably by between 10% and 95%.

A quantitative method for evaluating porosity distribution within a porous article, such as a porous rod, may comprise the steps of obtaining a digital image of a transverse area of the article, determining the pore area fraction present within each of a plurality of identically dimensioned sub-areas of the transverse area of the article, thereby obtaining a plurality of pore area fractions, and determining the standard deviation of the pore area fractions. The standard deviation of the pore area fractions in this case would be representative of the width of the porosity distribution. Each sub-area overlaps at least one adjacent sub-area, preferably by between 10% and 95%.

As used herein, a "transverse area of the article" relates to an area of an article that is in a plane generally perpendicular to the longitudinal dimension of the article. For example, the article may be a rod and the transverse area may be a cross-section of the rod taken at any length along the rod, or the transverse area may be an end face of the rod. The transverse area need not be taken from a plane that is exactly perpendicular to the longitudinal direction of the rod, but is preferably within about 45° of perpendicular to the longitudinal dimension of the rod. Preferably the transverse area is in a plane substantially perpendicular to the longitudinal direction of the rod.

As used herein, the term "pores" relates to regions of a porous article that are devoid of material. For example, a transverse area of a crimped filter will comprise portions of gathered sheet material and portions that are voids between the portions of gathered sheet material. Pores in this case relates to the voids between the sheet material.

As used herein, the term "porosity" refers to the volume fraction of void space in a porous article.

As used herein, the term "global porosity" refers to the fraction of pores in an entire cross-section of a porous article, for example a cross-section of a porous rod.

As used herein, the term "sub-area" refers to an area of the transverse area of the article that is smaller than the transverse area of the article and contains at least a portion of the transverse area of the article.

As used herein, the term "pore area fraction" refers to the fraction of pores within a sub-area. Pore area fraction is a measure of local porosity, that is the porosity within a sub-area. Another term for pore area fraction may be local porosity.

As used herein, the term "porosity distribution" refers to a measure of the variation in different pore area fractions. In other words, porosity distribution is a quantitative measure of the distribution of porosity over the transverse area of the article. As used herein "porosity distribution" and "local porosity distribution" have the same meaning. The width of the porosity distribution may be represented as the standard deviation in a plurality of pore area fractions.

A local porosity distribution, or porosity distribution, may be calculated solely from pore area fractions making up a single transverse area of an article. A local porosity distribution relating to any individual article may be compared with that of another individual article. The local porosity distribution may be seen to be a measure of the uniformity of porosity of an individual article. For example, if the standard deviation of a plurality of pore area fractions of an article is low, then the pores within the article are likely to be uniformly distributed over the transverse area of the article. If, however, the standard deviation of a plurality of pore area fractions of an article is high, then the pores are not uniformly distributed over the transverse area of the article.

A local porosity distribution, or porosity distribution, may be calculated from pore area fractions derived from transverse areas of a number of different articles, for example a set of articles. The local porosity distribution from a set of articles may be used to evaluate the quality of porosity between one set of articles and another.

As used herein, the terms "aerosol-generating article" and "smoking article" refer to an article comprising an aerosol-forming substrate that is capable of releasing volatile compounds that can form an aerosol. For example, an aerosol-generating article may be a smoking article that generates an aerosol that is directly inhalable into a user's lungs through the user's mouth. An aerosol-generating article may be disposable.

An aerosol-generating article or smoking article may be a heated smoking article, which is a smoking article comprising an aerosol-forming substrate that is intended to be heated rather than combusted in order to release volatile compounds that can form an aerosol. The aerosol formed by heating the aerosol-forming substrate may contain fewer known harmful constituents than would be produced by combustion or pyrolytic degradation of the aerosol-forming substrate.

As used herein, the term "aerosol-forming substrate" relates to a substrate capable of releasing volatile compounds that can form an aerosol. Such volatile compounds may be released by heating the aerosol-forming substrate. An aerosol-forming substrate may conveniently be part of an aerosol-generating article or smoking article. An aerosol-forming substrate may comprise, or be in the form of, a tobacco plug. For example, a tobacco plug formed from a gathered sheet of homogenised tobacco material may form an aerosol-forming substrate of an aerosol-generating article.

As used herein, a "crimped filter" relates to a filter formed by a process of crimping and gathering a sheet of filter material, for example a paper material or a polymer material, into a rod. The rod may be circumscribed by a wrapping material. A crimped filter has open pores in the longitudinal direction of the rod.

As used herein, a "tobacco plug" relates to a plug of tobacco formed by a process of crimping and gathering a sheet of processed or homogenised tobacco material into the form of a rod. The gathered tobacco material may be circumscribed by a wrapper, for example a cigarette paper, to form the tobacco plug. The tobacco plug has open pores in the longitudinal direction of the rod.

A porous article may be a porous rod. As used herein, the term "porous rod" refers to a rod or material that has open pores extending along a longitudinal dimension of the rod. A porous rod may be a crimped filter, or a tobacco plug or a conventional cigarette. A porous rod may have a diameter of between 5 mm and 10 mm, for example about 7 mm or about 8 mm.

The step of obtaining a digital image of a transverse area of the porous article may be carried out by any suitable method. For example, a transverse area of the porous article may be photographed using a digital camera or scanned using a scanner. A photograph may be taken using a conventional camera and the image produced may then be scanned and transformed into a digital image. A sub-area of the transverse area is an area that encompasses some, but not all, of the transverse area. The area of a sub-area is less than the area of the transverse area. The sub-area needs to be of a large enough size to be representative of the local morphology within the sub-area. The sub-area also needs to be small enough to detect local variations in porosity and density within the transverse area. In certain preferred embodiments, the width of the sub-area is between about one-fourth to one-tenth of the width of the porous article being measured. Where the transverse area of the article, such as a tobacco plug or filter rod segment is substantially circular, it is preferred that the sub-area of the rod is rectangular, having a height and width of the order of between one fifth of the plug diameter and one tenth of the plug diameter, for example of the order of one sixth of the plug diameter or one seventh of the plug diameter or one eighth of the plug diameter.

The pore area fraction of a sub-area is determined by dividing the area fraction of pores within the sub-area by the total area of the sub-area. Thus, the pore area fraction is the area fraction within the sub-area that represents voids divided by the total area of the sub-area.

As the plurality of pore area fractions are each calculated from identically dimensioned sub-areas of the transverse area, the plurality of pore area fractions may be used to evaluate the porosity distribution within the transverse area of the porous article. For example, parameters such as average pore area fraction and highest pore area fraction and lowest pore area fraction may be determined from the plurality of pore area fractions. The standard deviation of pore area fractions may be determined. Data relating to the porosity distribution may determine the uniformity of porosity within the transverse area of the porous article. As each sub-area overlaps with at least one adjacent sub-area it is ensured that representative pore area fractions are determined for the entire transverse area of the porous article.

Preferably the digital image of the transverse area consists of a plurality of pixels, and every pixel making up the transverse area is contained within at least one of the plurality of sub-areas. It is preferred that the digital image of the transverse area is at least 500 by 500 pixels.

It may be advantageous that each sub-area overlaps at least one adjacent sub-area by between 70% and 90%, for example about 80%.

The method may comprise the step of calculating the standard deviation of the plurality of pore area fractions. The standard deviation of pore area fractions may provide an indication of uniformity of porosity distribution within the porous article.

The method may be performed on more than one porous article at once. For example, a digital image may be obtained from each of a plurality of porous rods, the plurality of porous rods forming or being referred to as a set of rods, and the porosity distribution may be evaluated for the entire set of rods. A digital image may be obtained containing images of transverse areas of a plurality of porous rods, in which case the method may comprise the further step of detecting individual images of individual rods and manipulating the image to exclude pixels that do not fall within the transverse area of any of the plurality of porous rods.

It may be particularly advantageous for an image to be obtained of a plurality of porous rods simultaneously. For example, an end face of a plurality of cigarettes may be imaged and the image of each individual end face, being a transverse area, may be identified and selected using suitable image processing software.

It is preferred that the method is automated as much as possible. For example, it is preferred that method steps such as determining area, calculating the pore area fraction, and evaluating the porosity distribution are performed as processing steps by algorithms embodied in software.

The method may be particularly advantageous for determining the porosity distribution within a crimped filter, or a set of crimped filters. The method may also be particularly advantageous for determining or evaluating porosity distribution within a crimped and gathered tobacco plug, or a set of such plugs. The method may be particularly advantageous for determining proportion of loose ends in a conventional cigarette, or a set of cigarettes.

Thus, the method may be a method for evaluating porosity distribution within a continuous rod formed from a gathered sheet of material, for example a tobacco plug formed from or including a gathered sheet of tobacco material, or a filter or element formed from a gathered sheet of non-tobacco material such as polylactic acid. The continuous rod may comprise a sheet material selected from the group comprising a metallic foil, a polymeric sheet, and a substantially non-porous paper or cardboard. The continuous rod may comprise a sheet material selected from the group consisting of polyethylene (PE), polypropylene (PP), polyvinylchloride (PVC), polyethylene terephthalate (PET), polylactic acid (PLA), cellulose acetate (CA), and aluminium foil. The continuous rod may comprise a sheet material that is a non-porous paper or a biodegradable polymer such as polylactic acid or a grade of Mater-Bi® (a commercially available family of starch based copolyesters).

The transverse area of the continuous rod is a cross-section or end face of the continuous rod. The method comprises the steps of obtaining a digital image of a transverse area of the continuous rod, determining the area fraction of pores present within each of a plurality of identically dimensioned sub-areas of the transverse area, thereby obtaining a plurality of pore area fractions, and calculating the standard deviation of the plurality of pore area fractions to evaluate the porosity distribution within the transverse area of the porous article, in which each sub-area overlaps at least one adjacent sub-area by between 10% and 95%.

A second aspect of the invention may provide a method of controlling a process for manufacturing a porous article, such as a porous rod, comprising the steps of running a manufacturing process to produce at least one porous article, evaluating the porosity distribution within the at least one porous article using any method described above, and using the porosity distribution to control one or more process parameters of the process for manufacturing a further porous article. For example, the porosity distribution of the at least one porous article may be used to determine whether or not to vary one or more process parameters of the process for manufacturing a further porous article. It may be preferable to evaluate the porosity of more than one porous article at once. It may be advantageous if the evaluation of porosity within porous articles is determined on a regular basis, or a continuous basis, so as to provide constant feedback to the method of producing the porous articles.

The invention may provide a method for controlling the porosity of a porous article, such as a porous rod, comprising the steps of forming a porous article using a process for manufacturing a porous article, evaluating the porosity distribution within the at least one porous article using any method described above, and controlling one or more process parameters of the process for manufacturing a porous article to form further porous articles having a desired porosity distribution.

The process for manufacturing a porous article may be a process for manufacturing a crimped and gathered filter, the porous article being a rod of filter material. For example, the process for manufacturing the rod may involve the feeding of a sheet material through crimping rollers and then the gathering of the crimped sheet into a gathered continuous rod. The gathered continuous rod may be circumscribed by a wrapping to produce a continuous filter rod. This filter rod may then be sectioned to produce individual rods of filter material. In a method for controlling a process, individual filters produced may be periodically selected and the porosity distribution of the selected rods evaluated according to any method described above. The transverse area of the rod imaged for evaluation could be one or the other end of the filter perpendicular to the filters longitudinal direction.

The results of an evaluation of the porosity distribution within the filter may be indicative of the quality of the filter rods being produced by the manufacturing process. If the evaluated porosity deviates from a desirable level then parameters of the manufacturing process may be altered to change the porosity distribution. For example, the distance between crimping rollers may be changed, or the speed at which the sheet material is fed into the gathering means may be altered. By providing a feedback it may be possible to produce more consistent filters having uniform porosity distribution and desired properties.

The process for manufacturing the porous article may be a process for manufacturing a tobacco plug, and the porous article may therefore be a rod of tobacco. The formation of a tobacco rod or tobacco plug may be similar to that described above for the production of a filter material. For example, to produce a tobacco rod, a sheet of homogenised material may be fed through crimping rollers and gathered into a continuous rod. This continuous rod may be circumscribed by a wrapper and then sectioned to form individual tobacco rods or tobacco plugs. It may be particularly advantageous if the uniformity of tobacco plugs so produced can be monitored according to the invention and if the monitoring of the uniformity of porosity provides feedback to the manufacturing process for altering one or more parameters of the manufacturing process in order to improve the quality of the tobacco plugs so formed.

The process for manufacturing a porous article may be a cigarette manufacturing process, and the porous article may be a standard conventional cigarette. By monitoring the porosity of the ends of selected cigarettes, the manufacturing process parameters may be controlled to lead to a lower proportion of loose ends at the end of the cigarettes. This may improve the quality of the products produced.

Methods described above may be used to produce porous articles having predetermined properties. For example, certain properties of an article may be desirable, and a method of evaluating the porosity distribution may be used to provide feedback to enable a user to control processing parameters and produce articles having the desirable properties.

For example, it may be desirable to form a rod having longitudinal open pores, and it may be desirable for that rod to provide a certain predetermined filtration efficiency. By evaluating porosity distribution of rods as they are produced, it may be possible to control process parameters to obtain the predetermined filtration efficiency.

As a further example, where an article is formed from a tobacco material, such as a rod formed from one or more sheet of reconstituted tobacco, it may be desirable to specify a porosity of the article to provide predetermined levels of nicotine delivery during use of the article. By evaluating porosity distribution of tobacco articles as they are produced, it may be possible to control process parameters to obtain the predetermined nicotine delivery.

As a further example, where an article is a conventional cigarette formed from cut leaf tobacco, it may be possible to evaluate porosity distribution of at the ends of the cigarettes and feedback this information to control process parameters and reduce the proportion of loose ends.

A method of controlling a process for manufacturing a porous article or a method of controlling the porosity of a porous article may comprises the steps of comparing the evaluated porosity distribution with a reference porosity distribution and controlling one or more process parameters in response to the comparison.

Where the porous article is a rod formed from a gathered sheet of material, a method may comprise the step of obtaining a digital image of a transverse area of the rod, the transverse area being an end face of the rod, using a camera mounted in the production line for forming the rod such that porosity distribution of the rod can be evaluated in real time during manufacture. Alternatively, the evaluation of porosity distribution of the rod may be conducted after manufacture of the rod using an offline device comprising a digital image capturing means and a processing unit for evaluating porosity distribution of the rod. A batch of rods may be fed into such a device for evaluation of the porosity distribution of the rods or of the entire batch of rods.

A device for evaluating porosity distribution may be provided. The device may evaluate porosity distribution according to any method described above. The device may comprise means for capturing a digital image of a transverse area of the article and a processor for analysing the digital image and calculating the porosity distribution. The means for capturing a digital image is preferably a digital camera.

The device may comprise a light source for illuminating the transverse area of the article. For example, a light source may be a spotlight or a flash unit. It is preferred that the light source provides an even illumination of the porous articles. A preferred light source may be a ring light or a ring flash arranged around the lens of a camera or at a predetermined distance from the porous article to provide even illumination of the article.

The device may comprise a sensor for determining a position of the porous article and triggering means for capturing a digital image when the porous article is located at, or passing through, a predetermined position. For example, digital images may be obtained as the porous articles are being formed or while a product comprising the porous article is being assembled. A sensor may trigger the image capture when the porous article is appropriately positioned.

A device may be mounted inline in a production line for forming the porous article to evaluate porosity distribution of articles in real time. Alternatively, a device may be a stand-alone device.

Porous rods, such as tobacco plugs and filters, for smoking articles are manufactured at high speed as a continuous rod. This continuous rod is a tube-like article, which may be cut at certain points into smaller rod-like articles. For example, porous articles comprising a gathered sheet of tobacco for use in smoking articles are first manufactured as one long rod-shaped article, which, in a number of steps, is cut into the final rod length for incorporation into the smoking article. Rod-shaped articles in a production line are typically transferred by a drum or rolling element.

Rod-shaped porous articles may be manufactured, for example, using a commercial rod maker. The tube-like continuous article may be initially cut into regular segments, each having the size of more than one final rod-shaped article, for example a long rod comprising ten lengths of a final rod-shaped article, followed by one or more cutting steps to finally obtain the final-length rod-shaped article. At the output of such a rod making device, rods may pass through a rolling element before being deposited on a flat bend. A digital image of a transverse cross section of a rod may be made as the rod is output onto the flat bend. The transverse cross section will be an end face of the rod.

The linear speed of a rod maker can be 100 m/min or greater. For example the linear speed of a rod maker can be 150 m/min or 200 m/min. A digital image of a transverse section of a rod, or the rods, can be obtained using a digital camera. Preferably a high speed camera is used. In one specific embodiment, a suitable camera may be a Sony XCD-V60 with a relative shutter of 8 and a HF25SA objective opened at 2+5 mm extension. Other cameras may be used, for example a Sony XCD-SX90 with a HF25 objective, or HF35HA-1B objective. For porous rods having a diameter of about 7.5 mm, the resolution of the camera should be high enough to ensure that an image of the cross section of each porous rod is represented by at least about 500 by 500 pixels.

In one embodiment the camera is positioned horizontally in order to image end faces of the rods passing between the rolling element and the bend of a rod maker. As rods are placed precisely inside the rolling element, a constant distance between the end faces of the rods and the camera is obtained. A sensor may be used to control the shutter of the camera to obtain a digital image of the cross section of the rod when the rod is optimally positioned in front of the lens of the camera and exposing an end face. Alternatively, the shutter of the camera may be triggered by the rolling element.

Alternatively, the device may automatically position the rod in the correct position to capture a digital image. For porous rods having a diameter of about 7.5 mm, accuracy of the position should be at least ±0.2 mm.

Lighting of the end faces of the rods may be effected using a spot light, for example a Schott spotlight set up at an angle of 45°. Alternatively, a more powerful light source such as Volpi IntraLED 3 may be used.

A digital image of an end face of a rod may also be made on a combiner before assembly of the final product. For example, if a rod-shaped filter or tobacco plug is to be incorporated in a smoking article, an image of the end face of the rod-shaped filter or tobacco plug may be obtained during assembly of the smoking article. An image of the porous rod may also be obtained after assembly into the final product, for example when a cross section of the porous rod is exposed. To control quality of, for example, a smoking article comprising a tobacco rod and a filter, one or more digital images can be obtained, such as one end face to image the tobacco plug and the other end face to image the filter.

Certain porous materials such as, for example, filters may have reflecting cross-section surfaces. In order to obtain a quality digital image of a cross-section of such an article, homogeneous light is needed around the position where the cross section is exposed. Lighting can be through white light, for example a white light source LED Schott LSS A20960. Lighting can be set at different levels depending on the material forming the porous rods. For example, lighting levels may be set at 100% when a digital image of a rod comprising tobacco is captured, or at 30% in case of a filter material. Lighting may also be effected by means of a ring light, such as, for example, RingLight A08660 (Schott). Distance between the light source and the porous rod is preferably optimized according to source of light and material of rod. It will be obvious to a person skilled in the art that the light source and light power may need to be adapted based on the material of the porous article.

The porosity distribution within a porous rod can be calculated using a processor, for example by using a PC.

Feedback to the manufacturing device or production line for the porous article may be effected by adapting certain parameters of the production process such as, for example, the crimping of the input materials. For example, a filter containing polylactic acid may comprise a crimped and gathered sheet, and the feedback may alter the degree of crimping of the sheet that is performed prior to gathering. Feedback may also be made to automatically reject or eject porous articles that have porosity distributions that do not meet predetermined specifications. At an assembly line, feedback by the processor can be used to reject the final product.

The device preferably has a user interface such as for example a keyboard, a barcode reader or touch screen or other means to communicate with external data processing or programming equipment.

Specific embodiments of the invention will now be described with reference to the Figures in which.

A specific embodiment of the invention will now be described with reference to a method for evaluating porosity distribution within a tobacco plug.

Figure 1:
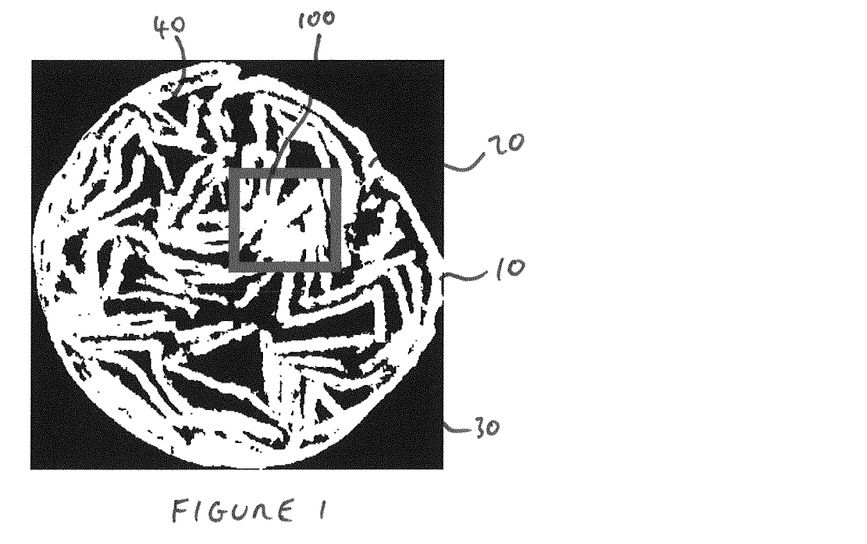
FIG. 1 is an image of a transverse area of a porous tobacco rod. The image is shown with a sub-area superimposed.

FIG. 1 illustrates an end face of a tobacco plug 10 formed by a process of crimping and gathering a sheet of homogenised tobacco material. The image of FIG. 1 is a digital image which has been processed such that all white pixels correspond to tobacco 20, black pixels outside the outer circumference of the rod 30 relate to the background, and black pixels within the circumference of the plug 40 correspond to pores. The image is obtained by taking an image of the end face of the tobacco plug and digitally processing the image of the transverse area of the plug to identify pixels that are within the transverse area of the rod. A threshold is then applied to the image such that pixels within the transverse area are either white, representing tobacco material, or black, representing pores. In FIG. 1, the tobacco plug is substantially circular and has a diameter of about 7 mm. The entire area within the outer circumference of the tobacco plug is the transverse area. FIG. 1 illustrates a first sub-area 100 positioned within the transverse area. The first sub-area is a rectangular area having dimensions of 1 mm by 1 mm.

In FIG. 1, the first sub-area 100 is illustrated in a position where the local porosity is low. In other words the pore area (the black pixels within the first sub-area 100 of FIG. 1) is small compared to the overall area of the first sub-area (1 $mm^2$).

Figure 2:
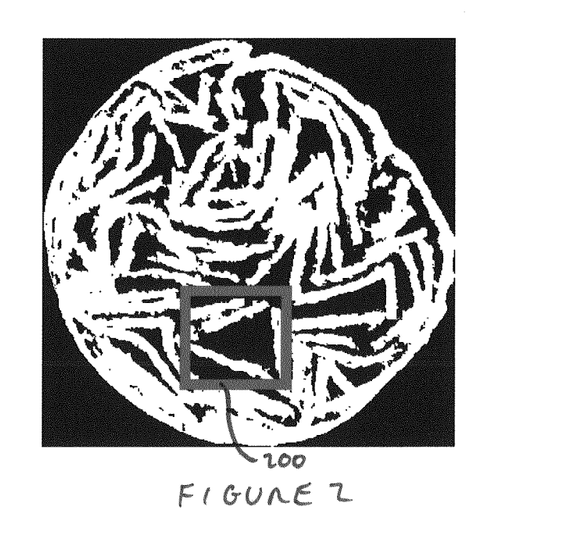
FIG. 2 is the transverse area of a tobacco rod illustrated in FIG. 1 showing a sub-area in a different portion of the transverse area.

FIG. 2 illustrates the same transverse area that is illustrated in FIG. 1. FIG. 2 shows a second sub-area 200 positioned in a region having a higher local porosity, as reflected by the higher pore area within the corresponding sub-area. Different sub-areas positioned in different regions of the transverse area will have different pore area fractions. By evaluating pore area fractions for multiple sub-areas within the transverse area, it is possible to obtain a porosity distribution.

Figure 4:
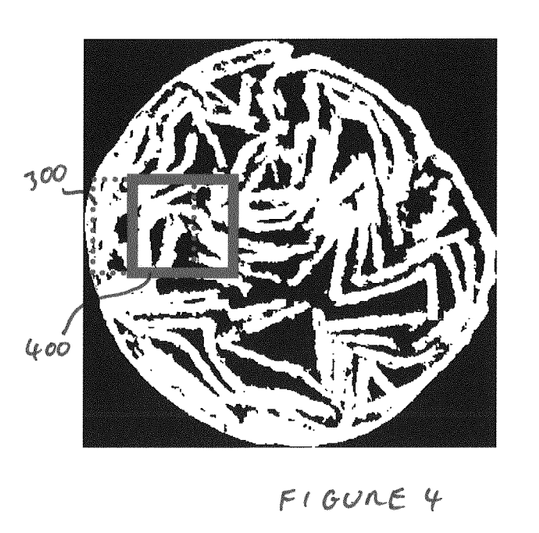
FIG. 4 illustrates the extent to which the sub-area of FIG. 3 is overlapped by a further sub-area.
Figure 5:
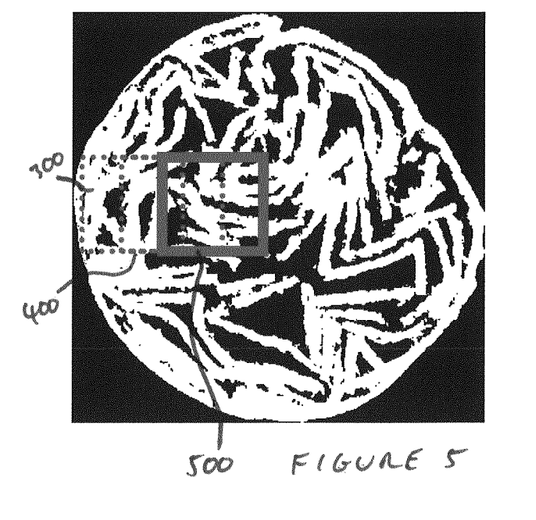
FIG. 5 illustrates the extent to which a further sub-area overlaps the sub-areas of FIG. 4.

The porosity distribution is obtained by computing the porosity locally (i.e., the pore area fraction) in each of the plurality of sub-areas. For each individual tobacco sub-area, the pore area fraction of a sub-area of the image, which may be referred to as local porosity, is calculated. Local porosity may be calculated by the formula $P_l = N_{voidlocal}/N_{local}$ where $P_l$ is the local porosity within the sub-area, $N_{voidlocal}$ is the number of pixels representing void space within the sub-area, and $N_{local}$ is the total number of pixels in the sub-area. Sub-areas are applied to and translated across the digital image of the rod by an iteration algorithm embodied in software. In order to obtain the plurality of local porosity readings, a sub-area is effectively translated through the image sequentially, and the local porosity calculated in each position that the sub-area occupies. Each position that the sub-area occupies overlaps with at least one other position occupied by the sub-area. This process is illustrated in FIGS. 3 to 5.

Figure 3:
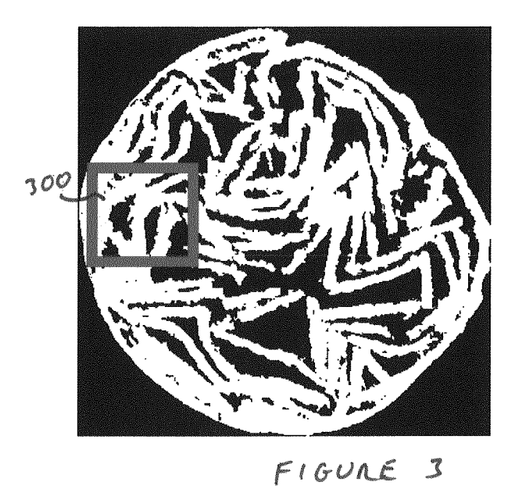
FIG. 3 is an image illustrating the transverse area of FIG. 1 and showing a sub-area in a third different portion of the transverse area.

FIG. 3 illustrates the transverse area of the tobacco plug with a third sub-area 300 superimposed on a left side of the plug. The local porosity is calculated in this sub-area. Then the sub-area is translated to the right across the transverse area. FIG. 4 illustrates a fourth sub-area 400 superimposed on the digital image of the tobacco plug. FIG. 4 also shows (in dotted lines) the position of the third sub-area 300. It can be seen that the fourth sub-area 400 overlaps with the position of the third sub-area 300. The local porosity is calculated in the fourth sub-area and the sub-area is again translated across the transverse area. FIG. 5 illustrates the transverse area showing a fifth sub-area 500. FIG. 5 also shows (in dotted lines) positions of the third 300 and fourth 400 sub-areas. A local porosity value is obtained for the fifth sub-area 500 and the sub-area is translated once more through the structure. This proceeds until all pixels within the structure have been included in one or more sub-areas.

Figure 6:
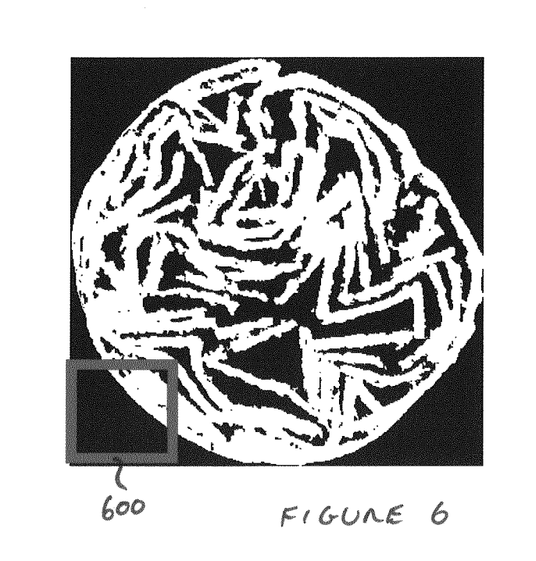
FIG. 6 illustrates the transverse area of FIG. 1 and shows a sub-area positioned so that most of the sub-area is not within the transverse area.

In the example here, the local porosity within a sub-area is only calculated if at least 90% of the pixels within the sub-area are also inside the transverse area. Preferably, at least 50% of the pixels within the sub-area are inside the transverse area. FIG. 6 illustrates the transverse area of the tobacco plug and shows a sixth sub-area 600 superimposed on the digital image. Fewer than 90% of the pixels of the sixth sub-area 600 lie within the transverse area, i.e. the area within the tobacco plug. Thus, the local porosity is not calculated with respect to the sixth sub-area. This is to avoid local porosity being calculated for sub-areas in which there is not a high enough area for the local porosity to be representative of the local tobacco structure.

Computed values of local porosity for each sub-area are stored in an array. The average value and standard deviation of the local porosity can then be calculated for the tobacco plug. The standard deviation of the local porosity can be used as a measure of the width of the porosity distribution. This gives a quantitative value of how uniform the tobacco is distributed in the plug. A low standard deviation indicates a uniform plug whereas a high standard deviation indicates a non-uniform plug.

The method may be used to calculate the porosity distribution of a plurality of tobacco plugs simultaneously. For example, a digital image may be obtained showing transverse areas of a plurality of tobacco plugs, and this digital image may be processed to identify each individual tobacco plug and obtain porosity distributions from each individual tobacco plug in the way described above. The porosity distribution may then be obtained for each individual tobacco plug and also for the plurality of tobacco plugs. As an example, a plurality of tobacco plugs may be placed on a flatbed scanner and scanned to produce a digital image showing an end face of each of the plurality of tobacco plugs. It is noted that the digital image acquisition may be done by any suitable method, for example by using digital cameras or computer tomography. The images may be represented by any suitable image format in full RGB (red-green-blue) colour, grey-scale, or binary (black and white) representations. Preferably the background in any image is uniform, to facilitate the detection and removal of the background during image processing. The resolution of any image should be high enough to accurately resolve the morphology of the tobacco plug.

After images are acquired, they may be converted to grey-scale if they are colour images and contrast may be adjusted to enhance the difference between regions of tobacco and regions of pores.

If the images are not already binary, then they are converted to binary. In a preferred embodiment, the negative of the image of a plurality of tobacco plugs is taken, in which black pixels represent solids and white pixels represent pores or void space, to facilitate automatic detection of tobacco plugs in the image. The connected black regions in the negative image, corresponding to the solid material in the tobacco plugs, are identified and labelled with a number, which is stored in a list. In one embodiment, the smallest possible rectangular bounding region is computed for each labelled connected black region. The area and aspect ratio of each rectangular bounding region is calculated, and connected black regions in rectangular bounding regions having a high or low aspect ratio are removed from the list. Because the tobacco plugs are substantially circular, each rectangular bounding region surrounding a tobacco plug should have an aspect ratio of about 1:1. All the detected black regions are then sorted in descending size so that regions representing tobacco plugs should come at or near the beginning of the list. Connected black regions in rectangular bounding regions having an area substantially above or below that expected for the article measured, i.e., tobacco plug, may be additionally removed from the list of connected black regions. In certain preferred embodiments, connected black regions in bounding regions having an area 50% larger or smaller than the expected area of the rectangular bounding region, or more preferably 30% larger or smaller than the expected area of the rectangular bounding region, are removed. The areas of the detected black regions can also be used as an alternative to the bounding regions. In alternative embodiments, the bounding region may assume a different shape such as circular; polygonal, such as octagonal, triangular, square, rhomboidal, etc.; or combinations thereof.

To confirm which regions on the list correspond to tobacco plugs, the variance of the region sizes may be optionally checked over the span of the expected number of plugs. For example, if the expected number of plugs in the image is given by the letter n, the size variance of the regions 1 to n in the list may be computed and stored in an array. Because the plug regions may not necessarily be the largest black regions in the negative image, the size variance computations is done for the regions 2 to n+1, 3 to n+2 etc. This is continued until the variance is measured across all connected black regions remaining in the list. To determine where in the list the first plug region appears, the minimum of the computed variances is identified. The regions corresponding to the other tobacco plugs should then be identifiable, since sizes of the plugs should be almost the same.

Individual plugs in an image of a set of plugs may be located by other means. A plurality of plugs making up a set of plugs may each have their own digital image, which negates the need to extract images of individual plugs.

A binary masking function may be used, where the tobacco plug has the value one, or in other words where the transverse area is and the area round the tobacco plug has the value zero.

Figure 7:
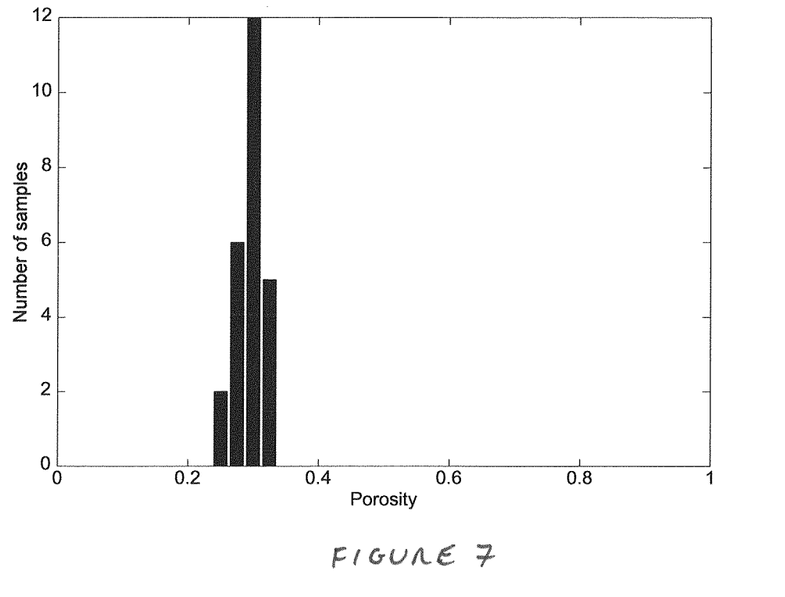
FIG. 7 is a graph illustrating the distribution of overall porosity in a set of tobacco plugs.

A porosity calculation may then be performed on each transverse area. The transverse area of each tobacco plug is converted to a binary image using a threshold value. In the binary image, the black pixels represent void space and the white pixels represent tobacco material. The overall porosity is calculated from the area fraction according to the equation: $P_o = N_{void}/N_{tot}$ where $P_o$ is the overall porosity of the transverse area, $N_{void}$ is the number of pixels representing void space within the transverse area and $N_{tot}$ is the total number of pixels in transverse area. For a set of tobacco plugs, the overall porosity derived from each plug may be plotted on a graph similar to that shown in FIG. 7. FIG. 7 shows that a set of tobacco plugs have an overall porosity of lying within a narrow distribution between 0.2 and 0.4.

Figure 8:
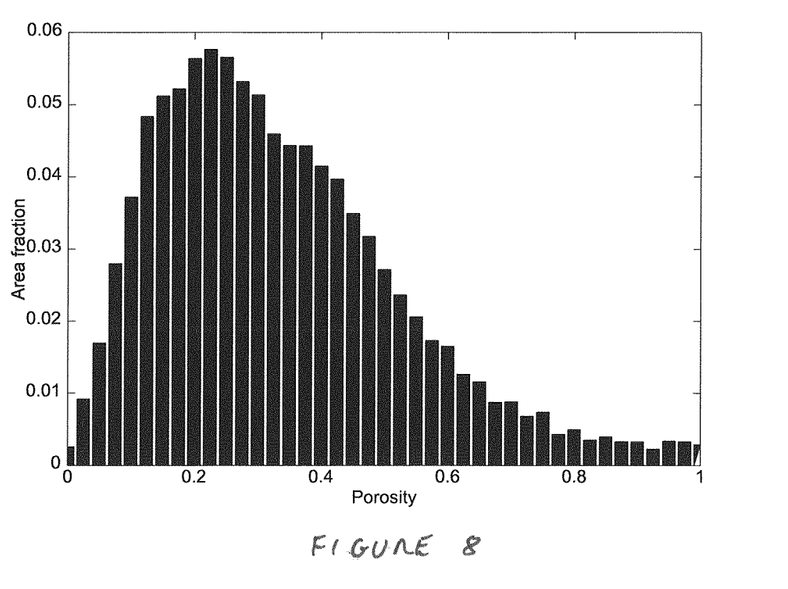
FIG. 8 is a graph illustrating the local porosity distribution for a set of tobacco plugs.

Porosity distribution can be calculated for each tobacco plug within the set according to a method as described above in relation to FIGS. 1 to 6. In addition to providing a porosity distribution for each individual plug, the overall porosity distribution for the set of plugs may be determined as shown in the graph of FIG. 8. The accumulated porosity distributions for different sets of tobacco plugs can be compared with each other to provide an indication of the difference in quality between different batches.

The results from a porosity evaluation as described above either in relation to an individual porous rod or a set of porous rods may be used to control a process for the manufacture of the porous rods. Thus, the method for evaluating porosity may provide feedback as to when process parameters are set so as to produce porous rods that are out of specification and allow the process parameters to be corrected to produce porous rods that are within allowable specification.

A device for evaluating porosity distribution of a porous article, such as a tobacco plug formed from a gathered sheet of tobacco material, or a filter formed from a gathered sheet of PLA, may be integrated as part of the porous article manufacture. A device for evaluating the porosity distribution requires an image capturing means, such as a digital camera, and a processor for performing the required processing steps to analyze a digital image obtained of the porous article. The device preferably further includes a light source for illuminating the porous article.

Figure 9:
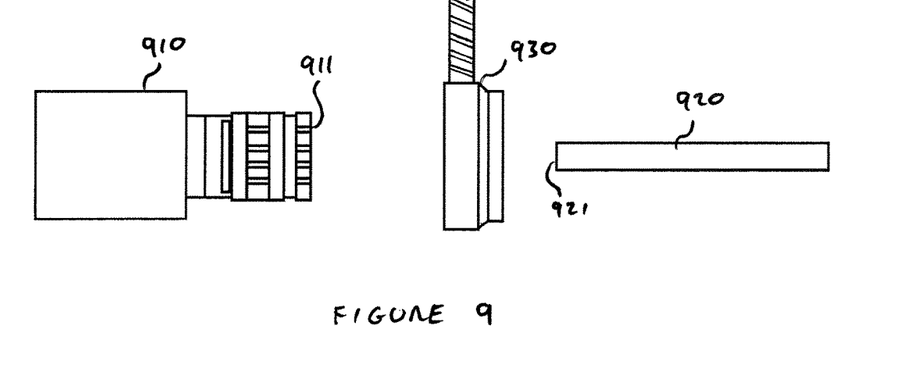
FIG. 9 is a schematic illustration of an image capture means for use in an online porosity distribution evaluation.

FIG. 9 illustrates a configuration of an image capturing means in which a camera 910 is arranged to capture a digital image of the end face 921 of a tobacco rod 920. The tobacco rod 920 is formed by crimping and gathering a sheet of homogenised tobacco material and circumscribing the gathered sheet with a wrapper to produce a rod. The lens 911 of the camera 910 is set to be a predetermined distance from the end face 921 of the tobacco rod 920.

In order to provide an even illumination of the end face 921 of the tobacco rod 920 a ring light 930, for example a Schott Ring Light A08660, is disposed between the camera lens 911 and the tobacco rod 920. The ring light 930 is preferably positioned closer to the tobacco rod 920 than the camera lens 911.

Figure 10:
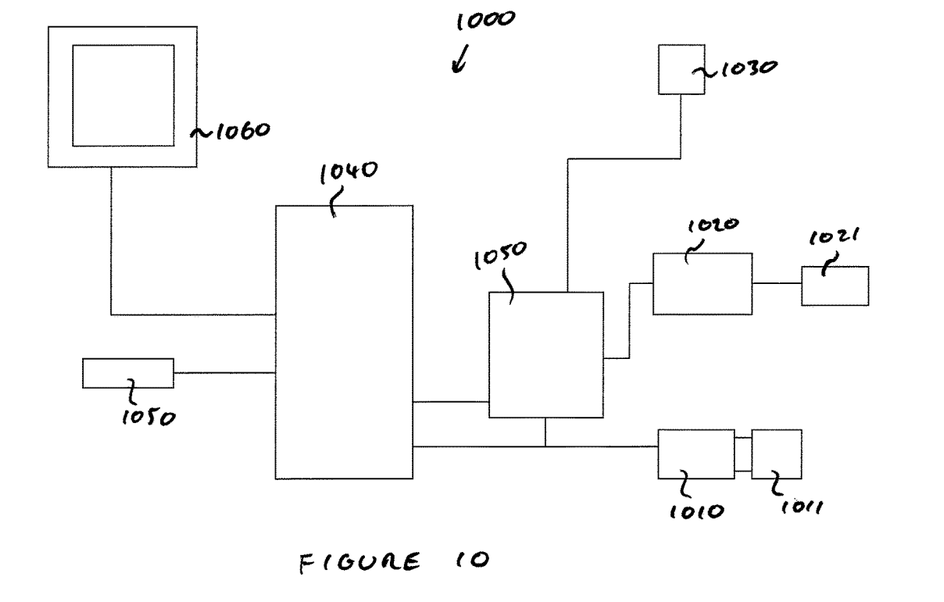
FIG. 10 is a schematic diagram illustrating the components of a device for performing an online porosity distribution evaluation.

FIG. 10 illustrates a device or system 1000 for evaluating porosity distribution of a porous rod, such as a tobacco rod. The device or system 1000 comprises a digital camera 1010 having a lens 1011, and a light source 1020 coupled to a ring light 1021. The shutter of the camera is controlled by means of a sensor 1030 that can detect the position of porous rods. Processing of the digital image obtained by the camera 1010 is performed by a processor within a PC 1040. The sensor, the light source, the camera, and the PC are linked together by a controller 1050. The PC further comprises a keyboard 1050 and a monitor 1060. A system or device having the components illustrated in FIG. 10 may be incorporated into a rod manufacture apparatus to evaluate the porosity distribution in rods in real time as they are formed. The system or device 1000 may be incorporated in a cigarette or smoking article assembly line, and evaluate porosity distribution in component parts of the cigarette or smoking article as the cigarette or smoking article is being assembled. The system or device having the components of FIG. 10 may, alternatively, form part of a stand-alone evaluation device for off-line assessment of the porosity distribution in batches of porous rods.

The invention claimed is:

1. A method for evaluating porosity distribution within a porous article, the method comprising the steps of:
    obtaining a digital image of a transverse area of the article;
    determining an area fraction of pores present within each of a plurality of identically dimensioned sub-areas of the transverse area, thereby obtaining a plurality of pore area fractions; and
    using the plurality of pore area fractions to evaluate the porosity distribution within the transverse area of the porous article,
    in which each sub-area overlaps at least one adjacent sub-area by between 10% and 95%.

2. The method according to claim 1 in which a standard deviation of the plurality of pore area fractions is calculated and a width of the porosity distribution is represented by the standard deviation of the plurality of pore area fractions.

3. The method according to claim 1 in which the digital image of the transverse area consists of a plurality of pixels, and every pixel making up the transverse area is contained within at least one of the plurality of sub-areas.

4. The method according to claim 3 in which the digital image of the transverse area is at least 500 by 500 pixels.

5. The method according to claim 1 in which each sub-area overlaps at least one adjacent sub-area by between 70% and 90%.

6. The method according to claim 1, in which the area fraction of any individual sub-area is only included for the evaluating porosity distribution if more than 50% of that sub-area is within the transverse area of the article.

7. The method according to claim 1, further comprising a step of determining a total area fraction of pores present within the transverse area of the article.

8. The method according to claim 1 in which the digital image is obtained from each of a plurality of articles, the plurality of articles forming a set of articles, in which porosity distribution is evaluated for the entire set of articles.

9. The method according to claim 8 in which the digital image is obtained containing images of transverse areas of a plurality of articles, the method further comprising a step of detecting images of individual articles and masking at least one of the images to exclude pixels that do not fall within the transverse area of any of the plurality of articles.

10. The method according to claim 1 in which the porous article is in the form of a rod having a plurality of open pores extending longitudinally through the rod.

11. The method according to claim 1 in which the porous article is a continuous rod formed from a gathered sheet of material comprising a tobacco plug formed from or including a gathered sheet of tobacco material, or comprising a filter or element formed from a gathered sheet of non-tobacco material comprising polylactic acid, the transverse area of the article being a cross-section or end face of the continuous rod.

12. A method of controlling a process for manufacturing a porous article comprising the steps of:
running a manufacturing process to produce at least one porous article;
evaluating a porosity distribution within the at least one porous article using a method according to claim 1; and
using the porosity distribution to control one or more process parameters of the process for manufacturing the porous article.

13. The method according to claim 12 in which the process for manufacturing the porous article is a cigarette manufacturing process and the porous article is a cigarette.

14. The method according to claim 13 in which process parameters are controlled to produce cigarettes with a lower proportion of loose ends.

15. The method according to claim 12 in which the process for manufacturing the porous article is a filter manufacturing process and the porous article is a rod of filter material.

16. The method according to claim 15 in which the porous article is a filter formed from a gathered sheet of material.

17. The method according to claim 12 in which the process for manufacturing the porous article is a tobacco plug manufacturing process and the porous article is a plug of tobacco.

18. The method according to claim 17 in which the plug of tobacco is formed from a gathered sheet of material.

19. The method according to claim 12 further comprising the steps of comparing the evaluated porosity distribution with a reference porosity distribution; and controlling one or more process parameters in response to the comparison.

20. The method according to claim 12 in which the porous article is a rod formed from a gathered sheet of material, and further comprising the step of obtaining a digital image of a transverse area of the rod, the transverse area being an end face of the rod, using a camera mounted in a production line for forming the rod such that a porosity distribution of the rod can be evaluated in real time during manufacture.

21. The method according to claim 12 in which the porous article is a rod formed from a gathered sheet of material, in which the evaluation of porosity distribution of the rod is conducted after manufacture of the rod using an offline device comprising a digital image capturing means and a processing unit for evaluating porosity distribution of the rod.

22. A method for controlling the porosity of a porous article comprising the steps of:
forming a porous article using a process for manufacturing a porous article;
evaluating a porosity distribution within the porous article using a method according to claim 1; and
controlling one or more process parameters of the process for manufacturing the porous article to form further porous articles, the further porous articles having a desired porosity distribution.

23. A method according to claim 1 to produce porous articles having a predetermined filtration efficiency.

24. A method according to claim 1 to produce a smoking article, or a tobacco plug for the smoking article, in which a local porosity distribution is controlled to provide a predetermined nicotine delivery during use of the smoking article.

25. A device for evaluating porosity distribution within a porous article using a method according to claim 1, the device comprising means for capturing a digital image of a transverse area of the article and a processor for analysing the digital image and calculating the porosity distribution.

26. The device according to claim 25, further comprising a light source for illuminating the transverse area of the article.

27. The device according to claim 25, further comprising a sensor for determining a position of the porous article and triggering the means for capturing the digital image when the porous article is located at, or passing through, a predetermined position.

28. The device according to claim 25 for mounting inline in a production line for forming the porous article to evaluate porosity distribution of articles in real time.

* * * * *